(12) United States Patent
Harrer et al.

(10) Patent No.: US 12,285,628 B2
(45) Date of Patent: Apr. 29, 2025

(54) INTELLIGENT OPTIMIZATION SETTING ADJUSTMENT FOR RADIOTHERAPY TREATMENT PLANNING USING PATIENT GEOMETRY INFORMATION AND ARTIFICIAL INTELLIGENCE

(71) Applicant: Brainlab AG, Munich (DE)

(72) Inventors: Christian Harrer, Munich (DE); Wolfgang Ullrich, Munich (DE)

(73) Assignee: BRAINLAB AG, Munich (DE)

( * ) Notice: Subject to any disclaimer, the term of this patent is extended or adjusted under 35 U.S.C. 154(b) by 737 days.

(21) Appl. No.: 17/429,839

(22) PCT Filed: Mar. 1, 2019

(86) PCT No.: PCT/EP2019/055201
§ 371 (c)(1),
(2) Date: Aug. 10, 2021

(87) PCT Pub. No.: WO2020/177844
PCT Pub. Date: Sep. 10, 2020

(65) Prior Publication Data
US 2022/0126116 A1 Apr. 28, 2022

(51) Int. Cl.
*A61N 5/10* (2006.01)
*G16H 20/40* (2018.01)

(52) U.S. Cl.
CPC ........... *A61N 5/1031* (2013.01); *G16H 20/40* (2018.01); *A61N 2005/1041* (2013.01); *A61N 5/1047* (2013.01); *A61N 2005/1074* (2013.01)

(58) Field of Classification Search
None
See application file for complete search history.

(56) References Cited

U.S. PATENT DOCUMENTS 9,507,886 B2 * 11/2016 Fiege .................... G06N 3/126
10,449,388 B2 * 10/2019 Yin ........................ A61N 5/103
(Continued)

FOREIGN PATENT DOCUMENTS

WO 2011153639 12/2011
WO 2014122567 8/2014
(Continued)

OTHER PUBLICATIONS

"Next generation arc therarpy for faster treatments, lower radiation dose to the patient" Elekta AB. 2014. 1 page.
(Continued)

*Primary Examiner* — Thomas R Artman
(74) *Attorney, Agent, or Firm* — Gray Ice Higdon

(57) ABSTRACT

By using the Al module, the method of the present invention calculates, i.e. predicts, the dependency $C_i$ ($p_i$) of a radiotherapy (RT) quality criterion C, from an adjustment of such a radiotherapy planning parameter $p_i$. In this way, the decision making process in RT treatment plan optimization is streamlined by prediction of promising settings of one or more radiotherapy planning parameters p, before the actual time intensive iterative optimization process is carried out. This is achieved by applying an Al module, which has been trained to predict the specific behaviour of the dose optimization algorithm, i.e. the optimizer, with respect to geometric patient data, dose prescription and treatment indication data. Thus, a computer-implemented medical method of predicting a dependency $C_i$ ($p_i$) of a radiotherapy (RT) quality criterion $C_i$ from an adjustment of a radiotherapy planning parameter p, is presented. The method comprises the following steps of providing geometric patient data geometrically describing an area of a patient, which is to be irradiated according to a radiotherapy treatment plan (step S1), providing dose prescription data and treatment indica-
(Continued)

tion data for said patient (step S2), and predicting with a trained Artificial Intelligence (AI) module the dependency $C_i$ ($p_i$) of the radiotherapy quality criterion $C_i$ from the radiotherapy planning parameter p, when adjusting said radiotherapy planning parameter $p_i$, thereby using the geometric patient data, the dose prescription data and the treatment indication data as input for the AI module (step S3).

17 Claims, 4 Drawing Sheets

(56) References Cited

U.S. PATENT DOCUMENTS

| | | | | |
|---|---|---|---|---|
| 10,512,790 | B2* | 12/2019 | Kuusela | A61N 5/1031 |
| 10,850,120 | B2* | 12/2020 | Laaksonen | A61N 5/1077 |
| 10,881,875 | B2* | 1/2021 | Ranganathan | A61B 6/5294 |
| 11,583,698 | B2* | 2/2023 | Yin | A61N 5/103 |
| 2013/0197878 | A1* | 8/2013 | Fiege | G06F 30/20 |
| | | | | 703/2 |
| 2016/0008630 | A1* | 1/2016 | Ranganathan | A61N 5/1031 |
| | | | | 600/1 |
| 2016/0129282 | A1* | 5/2016 | Yin | G16H 40/20 |
| | | | | 600/1 |
| 2018/0043182 | A1* | 2/2018 | Wu | A61N 5/1039 |
| 2018/0178036 | A1* | 6/2018 | Laaksonen | A61N 5/1031 |
| 2018/0193665 | A1* | 7/2018 | Kuusela | A61N 5/1031 |
| 2019/0038916 | A1* | 2/2019 | Ranganathan | A61B 6/5294 |
| 2020/0108276 | A1* | 4/2020 | Yin | G16H 40/20 |
| 2022/0126116 | A1* | 4/2022 | Harrer | G16H 20/40 |

FOREIGN PATENT DOCUMENTS

| | | |
|---|---|---|
| WO | 2016144914 | 9/2016 |
| WO | 2020177844 | 9/2020 |

OTHER PUBLICATIONS

"VMAT: RapidArc—Volumetric Arc Therapy" Varian Medical Systems, Inc. Retrieved from https://web.archive.org/web/20160402051327/http://varian.com/oncology/treatment-techniques/external-beam-radiation/vmat. 1 page.

International Search Report and Written Opinion for application PCT/EP2019/055201 dated Nov. 18, 2019.

* cited by examiner

INTELLIGENT OPTIMIZATION SETTING ADJUSTMENT FOR RADIOTHERAPY TREATMENT PLANNING USING PATIENT GEOMETRY INFORMATION AND ARTIFICIAL INTELLIGENCE

FIELD OF THE INVENTION

The present invention relates to a method of using Artificial Intelligence (AI) in radiotherapy (RT) treatment planning. In particular, the present invention relates to a computer-implemented medical method of predicting a dependency $C_i(p_i)$ of a radiotherapy quality criterion $C_i$ from an adjustment of a radiotherapy planning parameter $p_i$, a corresponding computer program, a non-transitory program storage medium storing such a program and a computer for executing the program, as well as a radiotherapy treatment planning system comprising the aforementioned computer.

TECHNICAL BACKGROUND

Radiotherapy treatment planning software available today already simplifies complex planning routines and provides access to sophisticated treatment options. For example, state of the art Monte Carlo dose algorithms generate highly faithful dose distributions within seconds for conformal beam and dynamic arc treatments, and for complex IMRT cases, within minutes. Seamless integration of such software allows its use with many different linear accelerators and multi-leaf collimator (MLC) types, virtually eliminating treatment area restrictions of conventional dose calculation algorithms.

In prior art radiotherapy treatment planning systems or software, like e.g. the Radiotherapy Treatment Planning Element Cranial/Spine (VMAT Planning), the optimization result, which generally is referred to as a "RT treatment plan", can typically be modified with slider controls by the user, depending on user preferences and demands. A typical example of the adjustments that can be made by the user with said sliders is adjusting the trade-off between e.g. the planning target volume (PTV) coverage and healthy tissue sparing. Such trade of is seen as "radiotherapy planning parameter $p_i$". Generally, for irradiation treatment planning in the field of radiotherapy and/or radiosurgery, a planning target volume associated with or representing e.g. a tumor, a metastasis and/or cancerous tissue or any other lesion to be treated, is specified along with a desired prescribed dose. The prescribed dose should preferably be deposited in at least a partial volume, also referred to as coverage volume, of the planning target volume in order to ensure biological effectiveness of the irradiation treatment. Apart from that, one or more constraints to be fulfilled during irradiation treatment can be specified by the user. Typically, an organ at risk, which preferably is to be spared during irradiation treatment or which should not receive more than an allowed dose in at least a partial volume thereof, can be specified as constraint. Based on the specified planning target volume, the prescribed dose and the one or more constraints, usually the coverage volume of the planning target volume is determined and a corresponding irradiation treatment plan is then calculated with an optimizer. This irradiation treatment plan can then be utilized to carry out the actual irradiation treatment at the patient.

Each treatment plan generated by the optimization process is optimal with respect to the current adjustments, i.e. said slider positions in the planning software with which a "radiotherapy planning parameter" can be adjusted, e.g. the trade-off between the planning target volume (PTV) coverage and healthy tissue sparing. However, since the optimizer, i.e. the algorithm calculating a treatment plan based on the slider positions chosen by the user, has to cope with contradicting goals, the global choice of the optimal plan for the specific patient is not clearly defined and has to be made by the user.

However, trying out every possible slider position and performing a complete optimization for each slider position can take a lot of time, e.g. up to 45 minutes depending on the complexity of the individual case. The inventors of the present invention identified that different optimization results might not differ much for a high number of different slider position configurations, which, however, cannot be foreseen by the user.

The inventors of the present invention have thus identified the need to streamline the decision making process in RT treatment plan optimization by prediction of promising settings for radiotherapy planning parameters $p_i$, e.g. promising slider positions in the RT planning software, before the actual time intensive iterative optimization process is accurately carried out by the optimizer.

It is, therefore, desirable to provide for an improved RT treatment planning, e.g. allowing to automatically and precisely predict whether changes in particular RT planning parameters $p_i$, often expressed and adjusted by said sliders of RT planning software, are likely to have a significant impact on one or more quality parameters or criteria $C_i$ of the treatment plan. The quality parameter or criterion $C_i$ may be seen as a characteristic of the optimization result, which to some extent are important for the user.

The present invention can be used for radiotherapy or radiosurgery procedures, such as the cranial/spine stereotactic radiosurgery treatment planning system, e.g. in connection with a system for image-guided radiotherapy such as VERO® and ExacTrac®, all products of Brainlab AG or TrueBeam of Varian.

Aspects of the present invention, embodiments, examples and exemplary steps are disclosed in the following. Different embodiments, examples and exemplary features of the invention can be combined in accordance with the invention wherever technically expedient and feasible.

Moreover, it is emphasized that any feature, element and/or step described in the following with respect to one aspect of the invention equally applies to any other aspect of the invention.

EXEMPLARY SHORT DESCRIPTION OF THE INVENTION

The present invention provides a new way of optimization setting adjustment for RT treatment planning using patient geometry information and Artificial Intelligence. In particular, the present invention provides for a computer-implemented medical method of predicting a dependency $C_i(p_i)$ of a radiotherapy (RT) quality criterion $C_i$ from an adjustment of a radiotherapy planning parameter $p_i$, as will be described in detail hereinafter.

The method of the present invention calculates, i.e. predicts, the dependency $C_i(p_i)$ of such a radiotherapy (RT) quality criterion $C_i$ from an adjustment of such a radiotherapy planning parameter $p_i$. In this way, the decision making process in RT treatment plan optimization is streamlined by prediction of promising settings of one or more radiotherapy planning parameters $p_i$ before the actual time intensive iterative optimization process is carried out. This is achieved by applying an Artificial Intelligence (AI) module, which has been trained to predict the specific behaviour of the dose optimization algorithm, i.e. the optimizer, with respect to geometric patient data.

In other words, the method predicts a dependency $C_i$ ($p_i$) of a radiotherapy quality criterion $C_i$ from an adjustment of a radiotherapy planning parameter $p_i$ based on input data, which comprise "geometric patient data", "prescription data" and "treatment indication data". These data are used as input for the AI module for the prediction of the dependency $C_i$ ($p_i$). Thus, this method allows predicting, i.e. calculating, whether in a certain case, for a specific patient geometry, dose prescription and area of the parameter space of RT planning parameter $p_i$, exploring the entire, possible range of the parameter $p_i$ with multiple optimizations is likely to change or significantly change a specific quality criterion $C_i$ of the resulting dose distribution, or not.

If, for example, the predicted dependency of $C_i$ ($p_i$) is nearly flat, i.e. the value of $C_i$ does not change or does not significantly change upon a variation of $p_i$ in a certain range, low number of anchor points may suffice. A corresponding example can be seen in FIG. 4. Then this result of the method of the present invention can be used to limit the range of the parameter $p_i$, in which the subsequent time intensive iterative optimization process is accurately carried out by the optimizer. Moreover, so called "anchor points", i.e. a specific set of values of $p_i$, can be determined by the presented method, which can be understood as selected values of $p_i$, which are used for the subsequent final time intensive iterative optimization process, instead of the entire range of $p_i$. In case of a dependency of $C_i$ ($p_i$), where $C_i$ strongly varies upon a variation of $p_i$ in a certain range, then this result of the method can be used for the final optimization process in that this range should be taken into account, and not neglected. Also this scenario will be elucidated further in the context of the embodiment of FIG. 4.

Generally, in this document the term "anchor points" thus refers to the specific $p_i$, e.g. the coordinates of the anchor in the parameter space. It should, however, be noted alternatively, "the anchor points" described herein could also be the dose distributions resulting from optimization with those specific $p_i$.

Therefore, the presented computer-implemented medical method of predicting a dependency $C_i$ ($p_i$) of a radiotherapy (RT) quality criterion $C_i$ from an adjustment of a radiotherapy planning parameter $p_i$ will save valuable time and calculation capacity in the overall process of finding the final treatment plan, which will be used to irradiate and treat the patient.

In general, the "radiotherapy quality criterion $C_i$" used in the present invention can be seen as a qualitative parameter indicative for a radiotherapy dose distribution. These radiotherapy quality criteria $C_i$ are typically used by the practitioner to evaluate a final 3D dose distribution that is achieved with a particular treatment plan. For example, the RT quality criterion $C_i$ can be the RT delivery time, a RT dose constraint, and/or a RT volume constraint regarding a volume within the patient. Other exemplary embodiments thereof will be given hereinafter. Furthermore, the "radiotherapy planning parameter $p_i$" is a parameter, which can typically adjusted by the user of the RT planning software in order to set constraints for the RT treatment plan and/or to define the RT treatment plan. A typical example is the trade of between the planning target volume (PTV) coverage and healthy tissue sparing. However, other exemplary embodiments of the "radiotherapy planning parameter $p_i$" are a weighting between a RT target and an organ at risk (OAR) and a parameter describing a degree of modulation in the dynamics of the RT treatment plan result. Further embodiments will be described in detail.

In the following, a short description of the specific features of the present invention is given which shall not be understood to limit the invention only to the features or a combination of the features described in this section.

GENERAL DESCRIPTION OF THE INVENTION

In this section, a description of the general features of the present invention is given for example by referring to possible embodiments of the invention.

According to a first aspect of the present invention a computer-implemented medical method of predicting a dependency $C_i$ ($p_i$) of a radiotherapy (RT) quality criterion $C_i$ from an adjustment of a radiotherapy planning parameter $p_i$ is presented. The method comprises the following steps:

providing geometric patient data geometrically describing an area of a patient, which is to be irradiated according to a radiotherapy treatment plan (step S1), providing dose prescription data and treatment indication data for said patient (step S2), and predicting with a trained Artificial Intelligence (AI) module at least a part of the dependency $C_i$ ($p_i$) of the radiotherapy quality criterion $C_i$ from the radiotherapy planning parameter $p_i$ when adjusting said radiotherapy planning parameter $p_i$, thereby using the geometric patient data, the dose prescription data and the treatment indication data as input for the AI module (step S3).

Generally, the presented method overcomes the drawback of the prior art RT planning approaches that the result or effectiveness of a variation/modification of a RT planning parameter $p_i$ is only seen after a full optimization is calculated by the optimizer. The presented method makes use of an AI module, which has learned with training data of previous patients, for which more or less full optimizations in the entire possible range of $p_i$ were done, how typically the dependency/relationship $C_i$ ($p_i$) was. These training data sets of said previous patients also contained geometric patient data, the dose prescription data and the treatment indication data for said patients. Such training data may be provided to the AI module as a so called "patient vector". Also the current data of the individual patient, for whom the presented method may be used, can be provided to the AI module in this form of the "patient vector". In a further embodiment the patient vector is an m-dimensional vector of numerical values.

Based on these three components of training data the AI module has learned how typically the relationship $C_i$ ($p_i$) is for a given data set. Based on the current input data of the individual patient, i.e. the current geometric patient data, the current dose prescription data and the current treatment indication data, the AI module can now identify a correlation with corresponding optimization results for "similar patients" that were contained in the training data. The dependency $C_i$ ($p_i$) for the current individual patient can be predicted by the AI module and furthermore, in an embodiment example promising values of $p_i$ and/or the corresponding slider positions in the treatment planning software, may be suggested to the user by this method. Such suggested "promising slider positions" are named "anchor points" in the context of the present invention. This will be explained in more detail hereinafter.

The term "geometric patient data" describes data of a single, individual patient. It may be a patient, who shall undergo a RT treatment and for whom a RT treatment plan shall be calculated using the presented method. It may also be a patient out of the training data set, for whom full optimization and determination of one or more dependencies $C_i$ ($p_i$) were calculated. These data geometrically describe the area of this patient, which shall be irradiated during the RT treatment. Geometrical features contained in "geometric patient data" may typically be one or more of the organ at risk (OAR) volume, the planning target volume (PTV), the distance OAR-PTV, OAR concavity/convexity, PTV concavity/convexity, overlap histogram (OVH) data, and others.

In an embodiment, the geometric patient data are obtained from image sets like CT or MR, or the like. In this embodiment organ structures are segmented from these images and the geometrical features are extracted and used as the geometric patient data.

As described before, these "geometric patient data" can be provided according to an exemplary embodiment in the form of a "patient vector", in which also the dose prescription data and the treatment indication data for said patient are contained.

The term "dose prescription data and treatment indication data" also describes data of a single, individual patient and defines with one or more parameters and/or constraints the dose of radiation and how it shall be irradiated to the patient's volume of interest. Exemplary parameters may be PTV dose prescription, PTV maximum dose, PTV minimum dose, OAR maximum dose, an OAR dose objective, a list of OARs, number of fractions, a highlighted, and a special OAR.

By predicting/calculating the dependency $C_i$ ($p_i$) based on the individual geometric patient data, the individual dose prescription data and the individual treatment indication data of the particular patient, the result of the method of the present invention can be used as knowledge, whether new/other values of the parameter $p_i$ are worth performing a full optimization for. This will be explained and elucidated with embodiment examples in more detail hereinafter.

The presented method may of course also use a plurality of current values of RT planning parameters $p_j$, that are different from $p_i$, and which represent the current slider positions of the other parameter the user can adjust with the RT treatment planning software. In this embodiment, these current values of RT planning parameters $p_j$ are considered by the AI module when predicting the dependency $C_i$ ($p_i$). This will become apparent from the explanations hereinafter, especially with regard to FIGS. 3 and 4.

It should be noted that the step S3 of predicting the dependency $C_i$ ($p_i$) by the trained AI module, as described hereinbefore and hereinafter, can be synonymously understood and used as follows. This step 3 may understood as providing the combination of the radiotherapy planning parameter $p_i$, the geometric patient data, the dose prescription data, and the treatment indication data, as input to the trained AI module, and obtaining, by inference using this AI module, the radiotherapy quality criterion $C_i$. Thus, it is clear to the skilled reader that $C_i$ depends at least on the radiotherapy planning parameter $p_i$, the geometric patient data, the dose prescription data, and the treatment indication data. This holds true for all embodiments mentioned herein, unless stated herein differently.

According to another exemplary embodiment the AI module has been trained using training input data sets comprising combinations of radiotherapy planning parameter $p_i$, geometric patient data, dose prescription data, and treatment indication data obtained from multiple real and/or simulated radiotherapy sessions on multiple patients, and at least one value or distribution of values of the radiotherapy criterion $C_i$ as ground-truth associated with each training input data set.

According to another exemplary embodiment the ground-truth value or distribution of values for $C_i$ has been obtained by dose optimization algorithm calculating a RT treatment plan.

According to another exemplary embodiment the AI module is configured as a classifier module and/or as a regressor module.

The term "artificial intelligence module" is an entity that processes one or more inputs into one or more outputs by means of an internal processing chain that typically has a set of free parameters. The internal processing chain may be organized in interconnected layers that are traversed consecutively when proceeding from the input to the output. Generally, the AI module may be seen as a computing unit and hence also the method step carried out by the AI module may be seen a computer implemented method step.

Many artificial intelligence modules are organized to process an input having a high dimensionality into an output of a much lower dimensionality. In the presented method, at least the geometric patient data, the dose prescription data and the treatment indication data are provided as an input for the AI module and the module outputs the dependency $C_i$ ($p_i$) or suggested anchor points, i.e. specific value of parameter $p_i$. The output may also comprise a probability that the dependency $C_i$ ($p_i$) is correct for the current patient.

Such a module is termed "intelligent" because it is capable of being "trained." The module may be trained using records of training data. A record of training data comprises training input data and corresponding training output data. The training output data of a record of training data is the result that is expected to be produced by the module when being given the training input data of the same record of training data as input. This systematic is used in the exemplary embodiment of the invention shown in FIG. 7. The deviation between this expected result and the actual result produced by the module is observed and rated by means of a "loss function". This loss function is used as a feedback for adjusting the parameters of the internal processing chain of the module. For example, the parameters may be adjusted with the optimization goal of minimizing the values of the loss function that result when all training input data is fed into the module and the outcome is compared with the corresponding training output data.

The result of this training is that given a relatively small number of records of training data as "ground truth", the module is enabled to perform its job, e.g., the prediction of the dependency $C_i$ ($p_i$), well for a number of records of input data that is higher by many orders of magnitude.

Many different AI modules can used for the present invention. Exemplary embodiments are (artificial) a neural network, a convolutional neural network, a generative adversarial network, a support vector machine, genetic algorithms, k-means, kernel regression discriminant analysis, and random forests.

A neural network is a prime example of an internal processing chain of an artificial intelligence module. It consists of a plurality of layers, wherein each layer comprises one or more neurons. Neurons between adjacent layers are linked in that the outputs of neurons of a first layer are the inputs of one or more neurons in an adjacent second layer. Each such link is given a "weight" with which the corresponding input goes into an "activation function" that gives the output of the neuron as a function of its inputs. The activation function is typically a nonlinear function of its inputs. For example, the activation function may comprise a "pre-activation function" that is a weighted sum or other linear function of its inputs, and a thresholding function or other nonlinear function that produces the final output of the neuron from the value of the pre-activation function.

A convolutional neural network is a neural network that comprises "convolutional layers". In a "convolutional layer", the output of neurons is obtained by applying a convolution kernel to the inputs of these neurons. This greatly reduces the dimensionality of the data. Convolutional neural networks are frequently used e.g. in image processing.

A generative adversarial network is a combination of two neural networks termed "generator" and "discriminator". Such a network is used to artificially produce records of data that are indistinguishable from records taken from a given set of training records of data. The generator network is trained with the goal of creating, from an input record with random data, an output record that is indistinguishable from the records in the set of training records. I.e., given that output record alone, it cannot be distinguished whether it has been produced by the generator or whether it is contained in the set of training records. The discriminator, in turn, is specifically trained to classify given records of data as to whether they are likely "real" training records or "fake" records produced by the generator. The generator and the discriminator thus compete against each other.

The AI module described herein has been trained with a high number of optimizations from other patients and can predict whether changes in particular parameters $p_i$/sliders are likely to have a significant impact on important characteristics $C_i$ of the optimization results such as PTV coverage percentage, maximum dose in most critical organ at risk (OAR) etc. This will be explained in more detail in the context of and elucidated with exemplary embodiments hereinafter.

In view of all the aspects and features explained hereinbefore, it can be concluded that the presented method provides for a mechanism to predict whether in a certain case, for a specific patient geometry, dose prescription and area of the parameter space, exploring the range of a specific radiotherapy planning parameter $p_i$ (i.e. a specific slider in typical RT treatment planning software) with multiple optimizations is likely to change a specific quality criterion C of the resulting dose distribution, or not. This is highly beneficial in RT planning since it safes valuable time and calculation capacity.

Rephrasing the first aspect of the present invention, the geometric patient data may be received, e.g. via a user input, and/or retrieved from a data storage device. Further, the does prescription data and treatment indication data may be received, e.g. via a user input, and/or retrieved from the data storage device. The trained AI module then determines, based on the knowledge it gained during the training phase with the training data of several data sets of previous patients and the calculated dose distributions and $C_i$ ($p_i$) dependencies, how the dependency $C_i$ ($p_i$) for the current patient most likely is. This output can beneficially be used for the next steps in finally determining the RT treatment plan, but without having to calculate with the optimizer dose distributions which are not helpful in determining the final RT treatment plan.

It is emphasized, that the invention solely relates to irradiation treatment planning. Accordingly, the invention does not involve or in particular comprise or encompass an invasive step which would represent a substantial physical interference with the body of a patient requiring professional medical expertise to be carried out and entailing a substantial health risk even when carried out with the required professional care and expertise. Particularly, the invention does not involve, comprise and/or encompass any surgical or therapeutic activity. The invention is instead directed as applicable to irradiation treatment planning before carrying out the actual irradiation treatment on the patient. For this reason alone, no surgical or therapeutic activity and in particular no surgical or therapeutic step is necessitated or implied by carrying out the invention.

According to another exemplary embodiment the method comprises the step of providing a start value of the radiotherapy planning parameter $p_i$, and wherein the step of predicting (S3) with the trained Artificial Intelligence (AI) module at least a part of the dependency $C_i$ ($p_i$) of the radiotherapy quality criterion $C_i$ from the radiotherapy planning parameter $p_i$ when adjusting said radiotherapy planning parameter $p_i$ starting from said start value thereby using the geometric patient data, the dose prescription data and the treatment indication data as input for the AI module (step S3).

According to another exemplary embodiment, the method further comprises the step:
determining a plurality of anchor points based on the predicted dependency $C_i$ ($p_i$) of the radiotherapy quality criterion $C_i$ from an adjustment of the radiotherapy planning parameter $p_i$, wherein each anchor point is a suggested value of said radiotherapy planning parameter $p_i$ for pre-calculating a dose distribution.

In this embodiment a suggestion in the form of "anchor points" is calculated for the user, which selected values of the radiotherapy planning parameter $p_i$ should be used for pre-calculating a dose distribution. Thus, the user may start the optimizer to do a full optimizations with only the predicted "anchor points" instead of the complete slider range. In other words, with this embodiment the slider positions with the most interesting "trade-offs" are predicted, as is exemplarily shown in FIG. 4. The anchor points may cover the entire range of the dependency $C_i$ ($p_i$) as is shown in both diagrams of FIG. 4. But they may also be the upper and lower limit of a range of the parameter $p_i$, which entire range is considered to be useful for the full optimisation, since in the entire range a full optimisation should be carried out.

Since optimization for even a single set of slider positions is a time consuming process, it has a massive time-saving effect to know beforehand if further optimizations in a specific area of the parameter space $p_i$ will change a criterion $C_i$ or not. In addition, a number of dose distributions (also called 'anchors') for certain slider positions are pre-calculated and the criterion values and dose distributions of unknown parameter sets can be approximated. The number of anchors needed for a good approximation is depending on the range of values achieved for $C_i$, a low range means low effectivity of a specific slider in that case and only a low number of pre-optimized dose distributions are needed while a high range demands for a more fine-grained approximation of the solution space. This systematic is also shown in FIG. 4.

Generally, the determination of the plurality of anchor points described herein can be carried out by the AI module, but can also be carried out by another calculation unit, which e.g. is part of a RT treatment planning system.

According to another exemplary embodiment the determination of the anchor points uses a comparison of the predicted dependency $C_i$ ($p_i$) with a predefined threshold.

In this embodiment it is further defined that for finding the anchor points the predicted dependency $C_i$ ($p_i$) is compared with a predefined threshold value. If for example, within a given range of $p_i$ defined by values $p_{i,1}$ and $p_{i,2}$ the difference between the maximum and minimum values of $C_i$ in this range is above this predefined threshold value than a relatively high number of anchor points is determined by the presented method. In this case the range of $p_i$ defined by values $p_{i,1}$ and $p_{i,2}$ is worth of "exploring" by calculating subsequently a full optimization with the optimizer for the relatively high number of anchor points. If, however, within a given range of $p_i$ defined by values $p_{i,1}$ and $p_{i,2}$ the maximum and minimum values of $C_i$ in this range is below this predefined threshold value than a relatively low number of anchor points is determined by the presented method. In other words, due to the dependency $C_i$ ($p_i$) predicted by the AI module, it is determined by the presented method that this range between $p_{i,1}$ and $p_{i,2}$ a detailed exploration in the sense of a full calculation/optimization of the treatment plan in this range is not needed. This embodiment and the logic thereof can easily be gathered from the exemplary embodiment of FIG. 5.

The previously described embodiments about the anchor points can particularly carried out while a plurality of current values of RT planning parameters $p_j$, that are different from $p_i$, are kept constant and are taken into account during the prediction by the AI module.

Similar to what is disclosed hereinbefore for the anchor points, in another related embodiment it is the change of the gradient of the curve $C_i$ ($p_i$) that is decisive for deciding how many anchor points are determined, as will be explained now.

According to another exemplary embodiment, the step of predicting the dependency $C_i$ ($p_i$) (S3) comprises
  determining whether within a predefined range of values of said radiotherapy planning parameter $p_i$ a change of a gradient of the dependency $C_i$ ($p_i$) is above or below a predefined threshold (S3b),
  determining a number of the plurality of anchor points depending on whether the change of the gradient of the dependency $C_i$ ($p_i$) is above or below the predefined threshold (S6).

In other words, this embodiment is limited to a method, in which the change of the gradient of the curve $C_i$ ($p_i$) is decisive for deciding how many anchor points are determined. If for example, within a given range of $p_i$ defined by values $p_{i,1}$ and $p_{i,2}$ the difference between the maximum and minimum values of the gradient of the dependency/curve $C_i$ ($p_i$) in this range is above this predefined threshold value than a relatively high number of anchor points is determined, since the range of $p_i$ defined by values $p_{i,1}$ and $p_{i,2}$ is worth of "exploring" by calculating subsequently a full optimization with the optimizer for the relatively high number of anchor points. If, however, within this range $p_{i,1}$ and $p_{i,2}$ the maximum and minimum values of the gradient of the dependency/curve $C_i$ ($p_i$) in this range is below this predefined threshold value than a relatively low number of anchor points is determined.

Generally, the additional method steps of this embodiment may be carried out by the AI module, but can also be carried out by another calculation unit, which e.g. is part of a RT treatment planning system.

According to another exemplary embodiment of the present invention a higher number of anchor points are determined when the change of the gradient of the dependency $C_i$ ($p_i$) is above the threshold as compared to a lower number of anchor points that are determined if the change of the gradient is lower than the predefined threshold.

According to another exemplary embodiment, the method further comprises the steps:
  pre-calculating a RT dose distribution for each of the determined anchor points (S7), and
  approximating a RT dose distribution, and preferably a value for the RT quality criterion $C_i$, for a value of the radiotherapy planning parameter $p_i$, which value is not an anchor point, thereby using results of the pre-calculation of the RT dose distribution for the anchor points (S8).

In this embodiment the dose distribution is calculated for the anchor points and these calculated dose distributions are used to approximate dose distributions and values of one or more RT quality criteria of unknown parameter sets. It should be noted that "calculating dose distributions" is used herein synonymously for the full optimization calculated by the optimizer. Thus, a number of dose distributions for the anchor points (i.e. for certain slider positions) are pre-calculated by the optimizer and the criterion values and dose distributions of unknown parameter sets are approximated by using these pre-calculated does distributions. Particularly this embodiment overcomes the drawback of the prior art RT planning approaches that the result or effectiveness of a variation/modification of a RT planning parameter $p_i$ is only seen after a full optimization, i.e. a full optimization for all or nearly all values of $p_i$, is calculated by the optimizer.

The additional method steps of this embodiment may be carried out by the optimizer as mentioned hereinbefore.

According to another exemplary embodiment the radiotherapy quality criterion $C_i$ is a qualitative parameter indicative for a radiotherapy dose distribution.

Moreover, according to a further exemplary embodiment of the invention the radiotherapy (RT) quality criterion $C_i$ is the RT delivery time.

According to an exemplary embodiment of the invention the radiotherapy (RT) quality criterion $C_i$ is a radiotherapy dosimetric criterion. In particular, the RT quality criterion Ci is selected from the group comprising complexity of RT quality assurance (QA), a RT dose constraint, a RT volume constraint regarding a volume within the patient, a conformity index describing how well an irradiated area correlates with a planning target volume (PTV), a gradient index describing how quickly a RT radiation dose decreases with increasing distance to a target volume, and any combination thereof.

A RT dose constraint may e.g. be a Planning Target Volume (PTV) dose prescription, a PTV maximum dose, a PTV minimum dose, a constraint for an Organ At Risk (OAR), an OAR maximum dose, an OAR dose objective, an allowed dose deposited in at least a partial volume of the OAR.

Further, it should be noted that RT quality assurance (QA) is a procedure carried out after having finally defined the treatment plan to be used, but before actually applying the radiation to the patient. A sensor array is used in this RT quality assurance procedure for detecting the radiation emitted by the radiation device thereby evaluating whether the real radiation beam corresponds to the desired beam defined by the treatment plan that was calculated. This procedure can be more or less complex depending on the radiation plan that was calculated. Hence, this RT quality assurance (QA) can be used as a RT quality criterion $C_i$.

According to an exemplary embodiment of the invention the radiotherapy planning parameter $p_i$ is selected from the group comprising a weighting between a RT target and an organ at risk (OAR), a parameter describing normal tissue sparing, a parameter describing a degree of RT modulation, and any combination thereof.

RT modulation as mentioned hereinbefore shall be understood as variability in dose rate during the RT treatment and/or variability in leaf travel during the RT treatment. As is known to the skilled reader, multi-leaf collimator (MLC) are nowadays used to shape and form the radiation beam of a RT treatment system. Said leaves are mechanically moving during the treatment to achieve that certain parts of the original radiation beam are blocked and other parts are transmitted towards the patient. This results in total in a movement pattern of the leaves.

Furthermore, the previously mentioned parameters $p_i$ are selected before the following general background of RT planning. The prescribed dose for the planning target volume (PTV) should preferably be deposited in at least a partial volume, also referred to as coverage volume, of the PTV in order to ensure biological effectiveness of the irradiation treatment. Apart from that, one or more constraints to be fulfilled during irradiation treatment are typically specified. Usually, an organ at risk, which preferably is to be spared during irradiation treatment or which should not receive more than an allowed dose in at least a partial volume thereof, can be specified as constraint. Based on the specified planning target volume, the prescribed dose and the one or more constraints, usually the coverage volume of the planning target volume is determined and a corresponding irradiation treatment plan is generated. In certain scenarios, however, a prescribed dose may not be deposited in a desired coverage volume of the planning target volume without affecting the organ at risk, and thereby potentially violating one or more of the specified constraints. This can, for instance, be the case if the planning target volume is located in vicinity of the organ at risk. Accordingly, a trade-off and compromise between the coverage volume of the planning target volume, in which a biologically effective dose is to be deposited, and a dose deposition or a sparing of the organ at risk should be found in order to, preferably, fulfil one or more constraints for the organ at risk. The radiotherapy planning parameter $p_i$ of this embodiment allow for a description of the desired constraints and trade-offs.

According to an exemplary embodiment of the invention the method comprises the steps
  determining an amended adjustment range of the RT planning parameter $p_i$ based on the predicted dependency $C_i(p_i)$, and
  suggesting the amended adjustment range to a user of an RT treatment planning software.

In this embodiment the adjustment range for the parameter $p_i$ is limited for the user. This embodiment does not limit to "sliders" only but covers any graphical representation of a "knob" with which the parameter can be adjusted by the user on a GUI of the RT treatment planning software.

Generally, the additional method steps of this embodiment can be carried out by the AI module, but can also be carried out by another calculation unit, which e.g. is part of a RT treatment planning system.

According to an exemplary embodiment of the invention the step of suggesting the amended adjustment range to a user further comprises:
  adapting a graphical user interface (GUI) of the RT treatment planning software such that the amended adjustment range of the RT planning parameter $p_i$ is displayed to the user.

In particular, slider or knob positions which are not likely to have a major effect on the optimization result are disabled. If desired, the user can be informed, which sliders will have the biggest impact on the optimization result in the specific case at hand.

In a further embodiment of the invention an adaptive parameter range covered by each slider customized to a specific patient case is established. If changes of a certain slider control already have a big impact, a more narrow range might be selected in order to get a more detailed view on the solution space. In another scenario, if the effects on the result are only marginal, the value range might be automatically extended or shifted.

The additional method steps of this embodiment can be carried out by the AI module, but can also be carried out by another calculation unit, which e.g. is part of a RT treatment planning system.

According to an exemplary embodiment of the invention the method comprises the step
  performing a full optimization of the RT treatment plan with the amended adjustment range of the RT planning parameter $p_i$ by using an RT planning optimization algorithm.

In this embodiment it is emphasized that a full optimization of the RT plan is calculated with the classical optimization algorithm, i.e. the optimizer, within the amended adjustment range found with the present invention. As mentioned before, the optimizer may be part of the RT treatment planning system, may also be part of e.g. an external computer, server.

According to an exemplary embodiment of the invention the steps of (S1) to (S3) are repeated for a plurality of RT quality criteria $C_i$ and a plurality of RT planning parameters $p_i$.

According to an exemplary embodiment of the invention the method comprises the step
  extracting geometrical features of the area of the patient, which is to be irradiated by radiotherapy, from at least one medical image and/or from organ structures segmented therefrom.

In this embodiment, the geometric patient data are obtained from image sets like CT or MR, or the like. In this embodiment organ structures are segmented from these images and the geometrical features are extracted and used as the geometric patient data. Segmentation is a well-known procedure for the person skilled in the art and is hence not described in greater detail here.

According to an exemplary embodiment of the invention the method comprises the steps
  providing said extracted geometrical features as an m-dimensional patient vector of numerical values, and
  using the m-dimensional patient vector as an input for the AI module.

Said m-dimensional patient vector of numerical values may be received, e.g. via a user input, and/or retrieved from a data storage device. In a further embodiment, the m-dimensional patient vector also comprises the dose prescription data and treatment indication data for said patient. In this case, also the input training data for the AI module resulting from various other patients and their treatment plans were provided to the AI module in the form of a m-dimensional patient vector. This will be explained in more detail in the context of FIGS. 5 and 6. Generally, the two previous embodiments describe how the patient data are created and used.

According to an exemplary embodiment of the invention the method comprises the steps
providing for a plurality of current values of RT planning parameters $p_j$, and
considering the current values of RT planning parameters $p_j$ when predicting the dependency $C_i(p_i)$ with the trained AI module.

The presented method may of course also use a plurality of current values of RT planning parameters $p_j$, that are different from $p_i$, and which represent the current slider positions of the other parameter the user can adjust with the RT treatment planning software. In this embodiment, these current values of RT planning parameters $p_j$, which differ from the parameter $p_i$, are considered by the AI module when predicting the dependency $C_i(p_i)$. This will become apparent from the explanations hereinafter, especially with regard to FIGS. 3 and 4. It should thus be noted that the previously described embodiments about the anchor points can particularly carried out while a plurality of current values of RT planning parameters $p_j$, that are different from $p_i$, are kept constant and are taken into account during the prediction by the AI module.

According to another exemplary embodiment of the invention the method comprises the step of providing and/or generating training data for the AI module and training the AI module with said training data.

In particular, the AI module can be trained with a high number of optimizations from other patients as is e.g. depicted in the embodiment of FIG. 7. Due to the training the AI module can then predict whether changes in particular sliders/parameters $p_i$ are likely to have a significant impact on important characteristics $C_i$ of the optimization results such as for example PTV coverage percentage, maximum dose in most critical organ at risk (OAR) etc. In general, the training of the AI module comprises the provision of several sets of geometric patient data, dose prescription data and treatment indication data as input for the AI module. Also the corresponding dependencies $C_i(p_i)$, that were previously calculated by an optimization with a classical RT treatment planning optimizer, are provided such that the AI module learns existing correlations between these three kinds of input data and the dependencies $C_i(p_i)$. This optimization with the classical RT treatment planning optimizer is shown in FIG. 7 with step "Optimization". This may of course be done for one or several RT quality criteria $C_i$ and one or more RT treatment planning parameters $p_i$.

In other words, the training data used comprises training input data, i.e. the geometric patient data, dose prescription data and treatment indication data, and corresponding training output data, i.e. the results $C_i(p_i)$ after the respective optimizations as exemplarily shown in FIG. 7. In general, the training output data of a record of training data is the result that is expected to be produced by the AI module when being given the training input data of the same record of training data as input.

The process of obtaining the data for training the AI module in one implementation is done automatically by running through a database of existing patient cases and treatment plans. Additional cases could be automatically added to this database, and the training process can be repeated in certain time intervals, so that the prediction quality of the presented method increases with time.

According to another aspect of the present invention a program is presented which, when running on a computer or when loaded onto a computer, causes the computer to perform the method steps of the method according to any one of the preceding embodiments or aspects;

and/or a program storage medium on which the program is stored;

and/or a computer comprising at least one processor and a memory and/or the program storage medium, wherein the program is running on the computer or loaded into the memory of the computer;

and/or a signal wave or a digital signal wave, carrying information which represents the program;

and/or a data stream which is representative of the program.

A computer program stored on a device, like e.g. a disc, is a data file, and when the file is read out and transmitted it becomes a data stream for example in the form of a (physical, for example electrical, for example technically generated) signal. The signal can be implemented as the signal wave which is described herein. For example, the signal and/or the signal wave is constituted to be transmitted via a computer network, for example LAN, WLAN, WAN, for example the internet. The invention according to this aspect therefore may alternatively or additionally relate to a data stream representative of the aforementioned program.

According to another aspect of the present invention a radiotherapy treatment planning system comprising the computer of the previous aspect.

According to another aspect of the present invention a radiotherapy treatment system is presented which comprises
a radiotherapy treatment planning system according to the previous aspect,
a radiation treatment apparatus comprising a treatment beam source and a patient support unit.
wherein the computer is operably coupled to the radiation treatment apparatus for issuing a control signal to the radiation treatment apparatus for controlling at least one of
the operation of the treatment beam source or
the position of the patient support unit.

According to another aspect of the present invention an AI module is presented which has been trained using training input data sets comprising combinations of radiotherapy planning parameter $p_i$, geometric patient data, dose prescription data, and treatment indication data obtained from multiple real and/or simulated radiotherapy sessions on multiple patients, and at least one value or distribution of values of the radiotherapy criterion $C_i$ as ground-truth associated with each training input data set.

Moreover, it is emphasized that features, functions, elements and/or steps, which are described above and in the following with reference to one aspect of the invention, equally apply to any other aspect of the invention described above and in the following. Particularly, features and/or steps, as described above and in the following, with reference to the method according to the first aspect, equally apply the computer program according to the second aspect, to the computer-readable medium according to the third aspect, to the computer according to the fourth aspect and/or to the medical system according to the fifth aspect, and vice versa.

These and other aspects of the invention will be apparent from and elucidated with reference to the embodiments described hereinafter.

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Providing Data

According to the present disclosure the terms providing data and retrieving data may be used synonymously. The expression "providing data" or "retrieving data" for example encompasses (within the framework of a computer implemented method) the scenario in which the data are determined by the computer implemented method or program. However, it also comprises receiving the data via e.g. a user input, and/or retrieving the data from a data storage device.

Determining data for example encompasses measuring physical quantities and transforming the measured values into data, for example digital data, and/or computing (and e.g. outputting) the data by means of a computer and for example within the framework of the method in accordance with the invention. The meaning of "providing data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "providing data" can therefore also for example mean waiting to receive data and/or receiving the data. The received data can for example be inputted via an interface. The expression "providing data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data provided by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the provision step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the provision step), the data can also be provided by performing the additional step of storing the data in a data storage medium (such as for example a ROM, RAM, CD and/or hard drive), such that they are ready for use within the framework of the method or program in accordance with the invention. The step of "providing data" can therefore also involve commanding a device to obtain and/or provide the data to be acquired. In particular, the provision step does not involve an invasive step which would represent a substantial physical interference with the body, requiring professional medical expertise to be carried out and entailing a substantial health risk even when carried out with the required professional care and expertise. In particular, the step of providing data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Treatment Beam

The present invention relates to the field of generating a treatment plan, based on which a treatment beam is controlled. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionizing radiation is for example used for the purpose of treatment. For example, the treatment beam comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumor are treated using ionizing radiation. The tumor is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

BRIEF DESCRIPTION OF THE DRAWINGS

In the following, the invention is described with reference to the appended figures which give background explanations and represent exemplary embodiments of the invention. The scope of the invention is however not limited to the specific features disclosed in the context of the figures, wherein.

The figures are schematic only and not true to scale. In principle, identical or like parts, elements and/or steps are provided with identical or like reference symbols in the figures.

DESCRIPTION OF EMBODIMENTS

Figure 1:
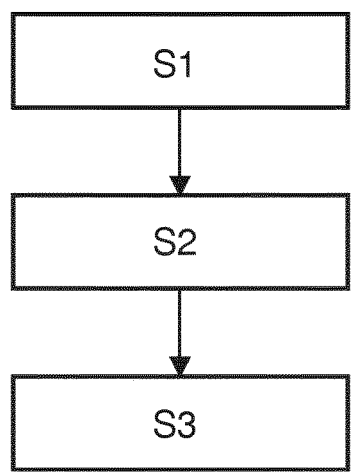
FIG. 1 shows a flowchart illustrating steps of a method of predicting a dependency $C_i$ $(p_i)$ of a radiotherapy (RT) quality criterion $C_i$ from an adjustment of a RT planning parameter $p_i$ according to an exemplary embodiment of the invention.

FIG. 1 shows a flow chart illustrating the basic steps of the method of predicting a dependency $C_i$ $(p_i)$ of a radiotherapy (RT) quality criterion $C_i$ from an adjustment of a radiotherapy planning parameter $p_i$, according to an exemplary embodiment and/or according to the first aspect.

The method of FIG. 1 is a computer-implemented medical method and comprises in step S1 the provision of geometric patient data geometrically describing an area of a patient, which is to be irradiated according to a radiotherapy treatment plan. Further, the provision of dose prescription data and treatment indication data for said patient is comprised as step S2. Predicting the dependency $C_i$ $(p_i)$ of the RT quality criterion $C_i$ from the RT planning parameter $p_i$ when adjusting said RT planning parameter $p_i$, thereby using the geometric patient data, the dose prescription data and the treatment indication data as input for the AI module forms step S3.

If desired, the steps of S1 to S3 are repeated for a plurality of radiotherapy quality criteria $C_i$ and a plurality of radiotherapy planning parameters $p_i$. Furthermore, it should be noted that in this and every other embodiment described herein the following additional steps may be comprised by the method. Providing for a plurality of current values, i.e. fixed values, of RT planning parameters $p_i$, and considering the current values of RT planning parameters $p_j$ when predicting the dependency Ci (pi) with the trained AI module.

Typically the "geometric patient data" comprise the organ at risk (OAR) volume, the planning target volume (PTV), the distance OAR-PTV, OAR concavity/convexity, PTV concavity/convexity, overlap histogram (OVH) data, and others. In an embodiment, the geometric patient data are obtained from image sets like CT or MR, or the like. In this embodiment organ structures are segmented from these images and the geometrical features are extracted and used as the geometric patient data. As described before, these "geometric patient data" can be provided according to an exemplary embodiment in the form of a "patient vector", in which also the dose prescription data and the treatment indication data for said patient are contained. Such a "patient vector" will be described in the context of FIG. 7 in more detail. Furthermore, typically the "dose prescription data and treatment indication data" comprise one or more of the PTV dose prescription, the PTV maximum dose, the PTV minimum dose, the OAR maximum dose, an OAR dose objective, a list of OARs, a number of fractions, a highlighted, a special OAR, and others.

The presented method of predicting a dependency $C_i$ $(p_i)$ will save valuable time and calculation capacity in the overall process of finding the final treatment plan, which will be used to irradiate and treat the patient.

If, for example, the predicted dependency of $C_i$ $(p_i)$ is nearly flat, i.e. the value of $C_i$ does not change or does not significantly change upon a variation of $p_i$ in a certain range. Such an example can be seen in FIG. 4. Than this result of the method of the present invention can be used to limit the range of the parameter $p_i$, in which the subsequent time intensive iterative optimization process is accurately carried out by the optimizer. Moreover, so called "anchor points", i.e. specific values of $p_i$, can be determined with the method of FIG. 1. Said "anchor points" can be understood as selected values of $p_i$, which are used for the subsequent final time intensive iterative optimization process, instead of the entire range of $p_i$. In case of a dependency of $C_i$ $(p_i)$, where $C_i$ strongly varies upon a variation of $p_i$ in a certain range, than this result of the method can be used for the final optimization process in that this range should be taken into account, and not neglected. Also this scenario will be elucidated further in the context of the embodiment of FIG. 4. Aspects about the training data of the trained AI module have been described before and are supplemented by the disclosure about FIG. 7.

In the following, a further detailed embodiment of the method of FIG. 1 is explained by means steps S1 and S3 as explained before and by means of additional method steps.

Figure 7:
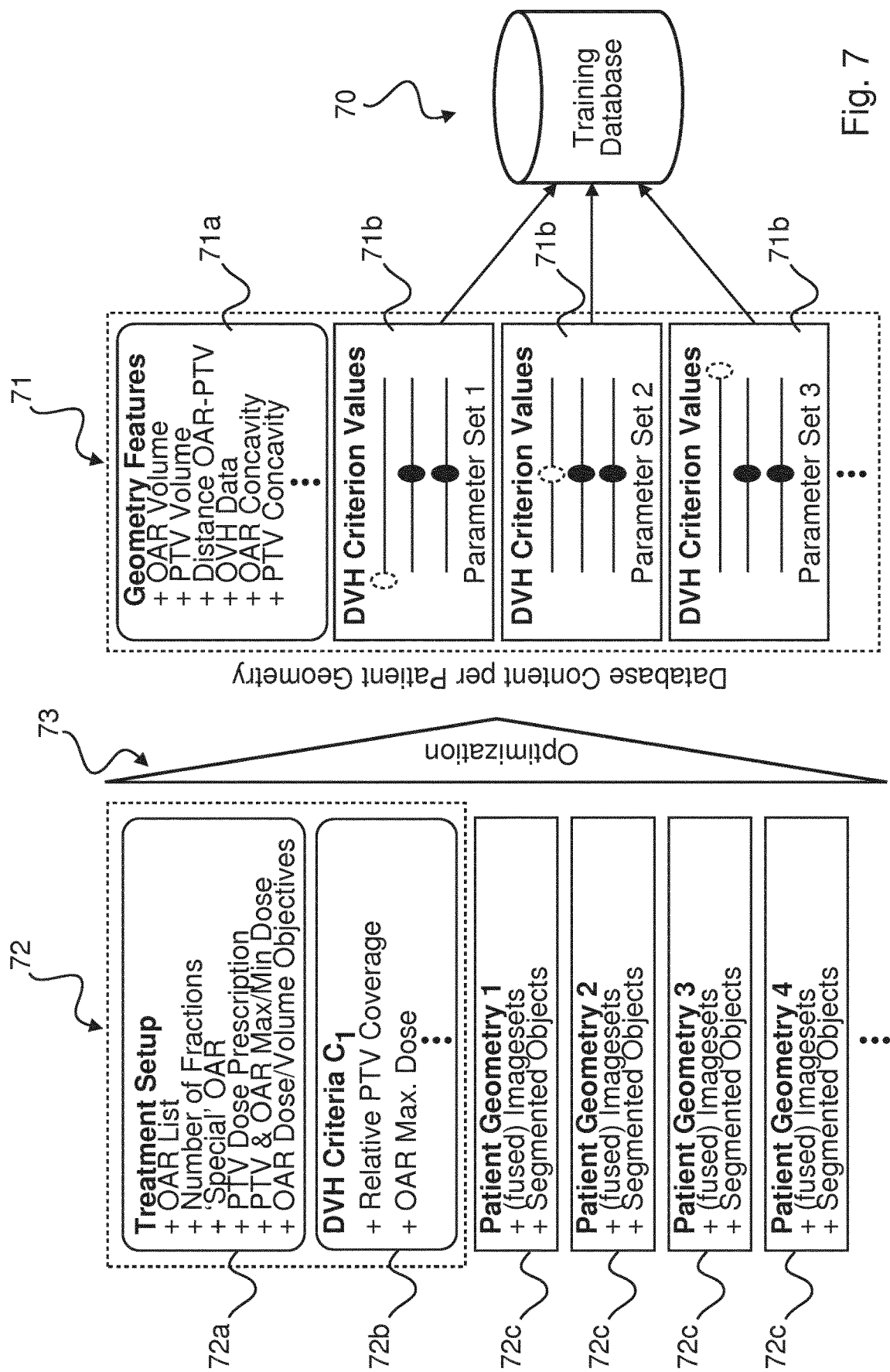
FIG. 7 schematically shows a method step of generating training data for the AI module according to another exemplary embodiment of the invention.

According to this further embodiment, in a first step a database of patient geometry data, dose prescription and treatment indication data and slider position configurations with characteristics of resulting treatment plans including dependencies $C_i$ $(p_i)$ is created. An embodiment of this database creation is shown in FIG. 7. In a further step the AI module is trained to predict slider positions, which create the biggest or minimum "trade-offs" in crucial dosimetric features $C_i$ of resulting treatment plans. For the current patient case of interest, geometric information from this patient case is extracted, typically by feature segmentation from medical images like CT or MRI images. Based on the geometric patient data, dose prescription and treatment indication data values of $p_i$ are determined which are most value to later on efficiently generate the final RT treatment plan. Thus, calculations are avoided in the subsequent optimization by the optimizer, which make us of values of $p_i$, which cost calculation time but do not or not significantly change the outcome of the RT treatment plan. Afterwards, full optimizations of the adjustment range of the predictions instead carrying out the optimization in the whole possible range of $p_i$. As a final step, the user may choose the final treatment plan, that is to be applied to the RT treatment system to initiate the treatment.

Figure 2:
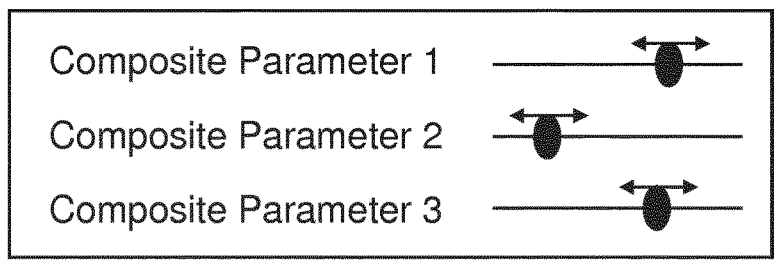
FIG. 2 schematically shows three different sliders/RT planning parameter $p_i$ modifiable by user via a typical graphical user interface of a RT treatment planning system.

FIG. 2 schematically shows three different sliders/RT planning parameter $p_i$ modifiable by user via a typical graphical user interface of a RT treatment planning system. The radiation dose distribution used for patient treatment is acquired by a computerized optimization algorithm, as has been explained before. Characteristics of this dose distribution can be influenced by adjustment of a number of optimization parameters $p_i$ via slider controls prior to optimization. Each single one of these parameters influences a whole group of various aspects of the optimization process. These 'composite' parameters are chosen in such a way that each parameter describes an important aspect of the optimization result, e.g. the trade-off between irradiating as much of the target volume as possible vs. putting emphasis on sparing the healthy tissue surrounding the target. Another example is: simple QA and fast delivery vs. an optimal dose distribution at the cost of higher delivery time and a more challenging QA process. An illustration on how these parameters can be adjusted in a graphical user interface is shown in FIG. 2.

Figure 3:
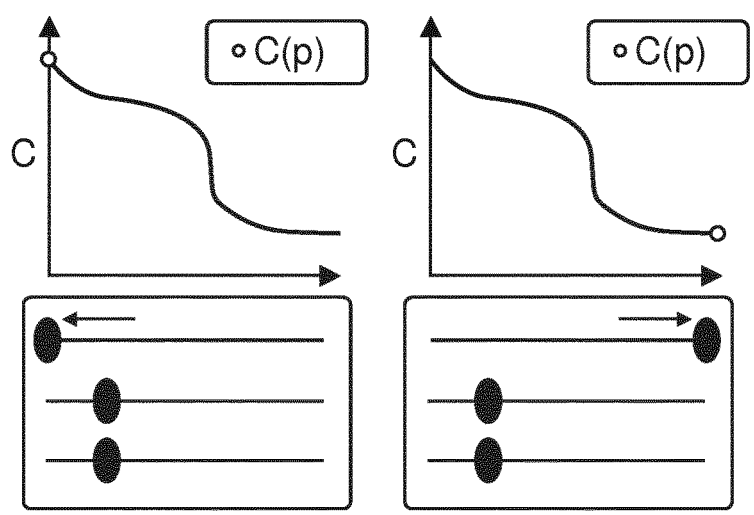
FIG. 3 schematically shows an example on how a specific RT quality criterion $C_i$ might change when one slider is moved through the whole value range without changing the remaining parameters.

FIG. 3 schematically shows an example on how a specific RT quality criterion $C_i$ might change when one slider is moved through the whole value range without changing the remaining parameters. Typically, the resulting 3D dose distribution is evaluated by a number of quality criteria $C_i$. Such a criterion can e.g. be a dose/volume constraint defined in the dose prescription or the conformity index (CI), or the gradient index (GI), as has been described in detail hereinbefore. Even though the value composition of the parameter values is initialized in way that gives a good effectivity for most cases, the direct behaviour of a specific $C_i$ depends on so many aspects (geometry of the patient, dose prescription and dosimetric optimization targets, the nature of the optimizer itself) that an analytical a priori statement on the behaviour of a specific $C_i$ with respect to changes in a specific slider cannot be made. However, the present invention overcomes this disadvantage as was explained before and is made even clearer with the following disclosure.

Figure 4:
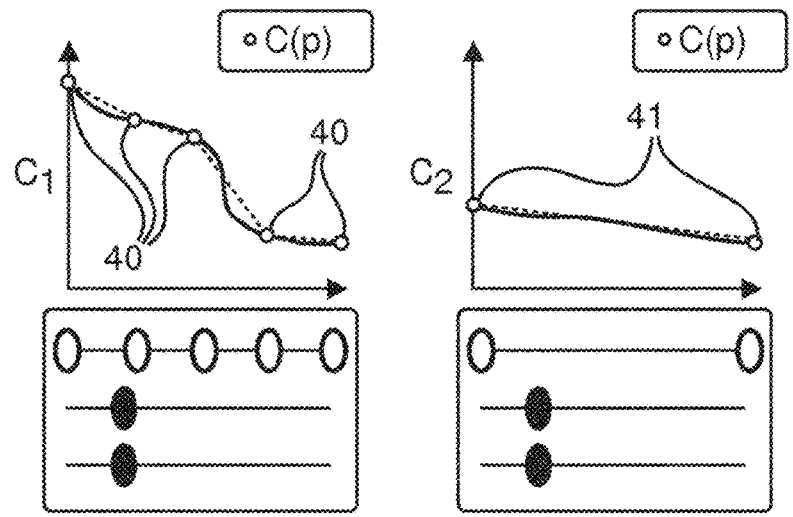
FIG. 4 schematically shows that the number of anchor points needed for a good approximation is depending on the range of values achieved for a $C_i$, which is used in another exemplary embodiment of the invention.

FIG. 4 shows an approximation resolution for two different RT quality criteria $C_i$ and $C_2$. In particular, FIG. 4 schematically shows that the number of anchor points 40, 41 needed for a good approximation is depending on the range of values achieved for a $C_i$. This insight is used in another exemplary embodiment of the invention. In said embodiment a plurality of anchor points is determined based on the predicted dependency $C_i$ ($p_i$) of the radiotherapy quality criterion $C_i$ from an adjustment of the radiotherapy planning parameter $p_i$. Therein each anchor point 40, 41 is a suggested value of said radiotherapy planning parameter $p_i$ for pre-calculating a dose distribution. Thus, the user may start the optimizer to do a full optimizations with only the predicted "anchor points" 40, 41 instead of the complete slider range. In other words, with this embodiment the slider positions with the most interesting "trade-offs" are predicted. The anchor points may cover the entire range of the dependency $C_i$ ($p_i$) as is shown in both diagrams of FIG. 4. But they may also be the upper and lower limit of a partial range of the parameter $p_i$.

Figure 5:
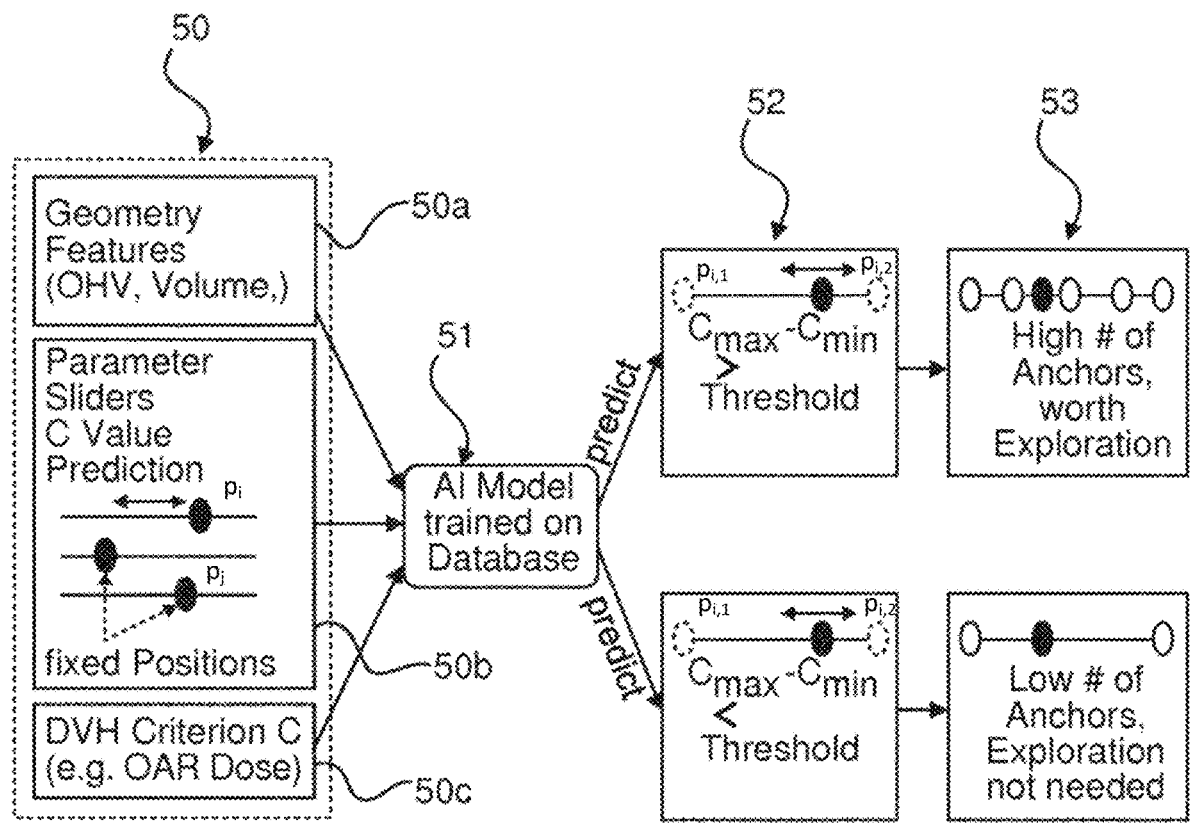
FIG. 5 schematically shows a method of predicting with a trained AI module the dependency $C_i$ $(p_i)$ and of determining a plurality of anchor points based on the predicted dependency $C_i$ $(p_i)$ of the RT quality criterion $C_i$ according to an exemplary embodiment of the invention.

FIG. 5 schematically shows a method of predicting with a trained AI module the dependency $C_i$ ($p_i$) and the method also determines a plurality of anchor points based on the predicted dependency $C_i$ ($p_i$) of the RT quality criterion $C_i$ according to an exemplary embodiment of the invention. This embodiment builds on FIG. 1 and comprises additional further features. As can be gathered from FIG. 5, the patient vector 50 comprises geometric patient data, dose prescription data and treatment indication data 50a. The patient vector 50 also describes, which radiotherapy planning parameter $p_i$ shall be varied/modified and defines fixed positions or values of the remaining radiotherapy planning parameter $p_j$, see reference sign 50b. Thus, in this embodiment a plurality of fixed values of RT planning parameters $p_j$ are provided and the fixed values of RT planning parameters $p_j$ are considered by the trained AI module when predicting the dependency $C_i$ ($p_i$). The patient vector 50 also defines, which RT quality criterion $C_i$ is selected by the user. This patient vector 50 may be used as input for the trained AI module/model 51, which predicts the values of RT quality criterion $C_i$ in the possible range of $p_i$. The AI module also determines the number of anchor points, thereby using a comparison of the predicted values of RT quality criterion $C_i$/the predicted dependency $C_i$ ($p_i$) with a predefined threshold.

If for example, within a given range of $p_i$ defined by values $p_{i,1}$ and $p_{i,2}$ the difference between the maximum and minimum values of $C_i$ in this range is above this predefined threshold value than a relatively high number of anchor points is determined by the presented method. In this case the range of $p_i$ defined by values $p_{i,1}$ and $p_{i,2}$ is worth of "exploring" by calculating subsequently a full optimization with the optimizer for the relatively high number of anchor points. If, however, within a given range of $p_i$ defined by values $p_{i,1}$ and $p_{i,2}$ the maximum and minimum values of $C_i$ in this range is below this predefined threshold value than a relatively low number of anchor points is determined by the presented method. In other words, due to the dependency $C_i$ ($p_i$) predicted by the AI module 51, it is determined by the presented method that this range between $p_{i,1}$ and $p_{i,2}$ a detailed exploration in the sense of a full calculation/optimization of the treatment plan in this range is not needed.

Similar to the previously mentioned embodiment, in a further embodiment it is determined whether within a predefined range of values of said radiotherapy planning parameter $p_i$ a change of a gradient of the dependency $C_i$ ($p_i$) is above or below a predefined threshold. Furthermore, the number of the plurality of anchor points is determined depending on whether the change of the gradient of the dependency $C_i$ ($p_i$) is above or below the predefined threshold.

Figure 6:
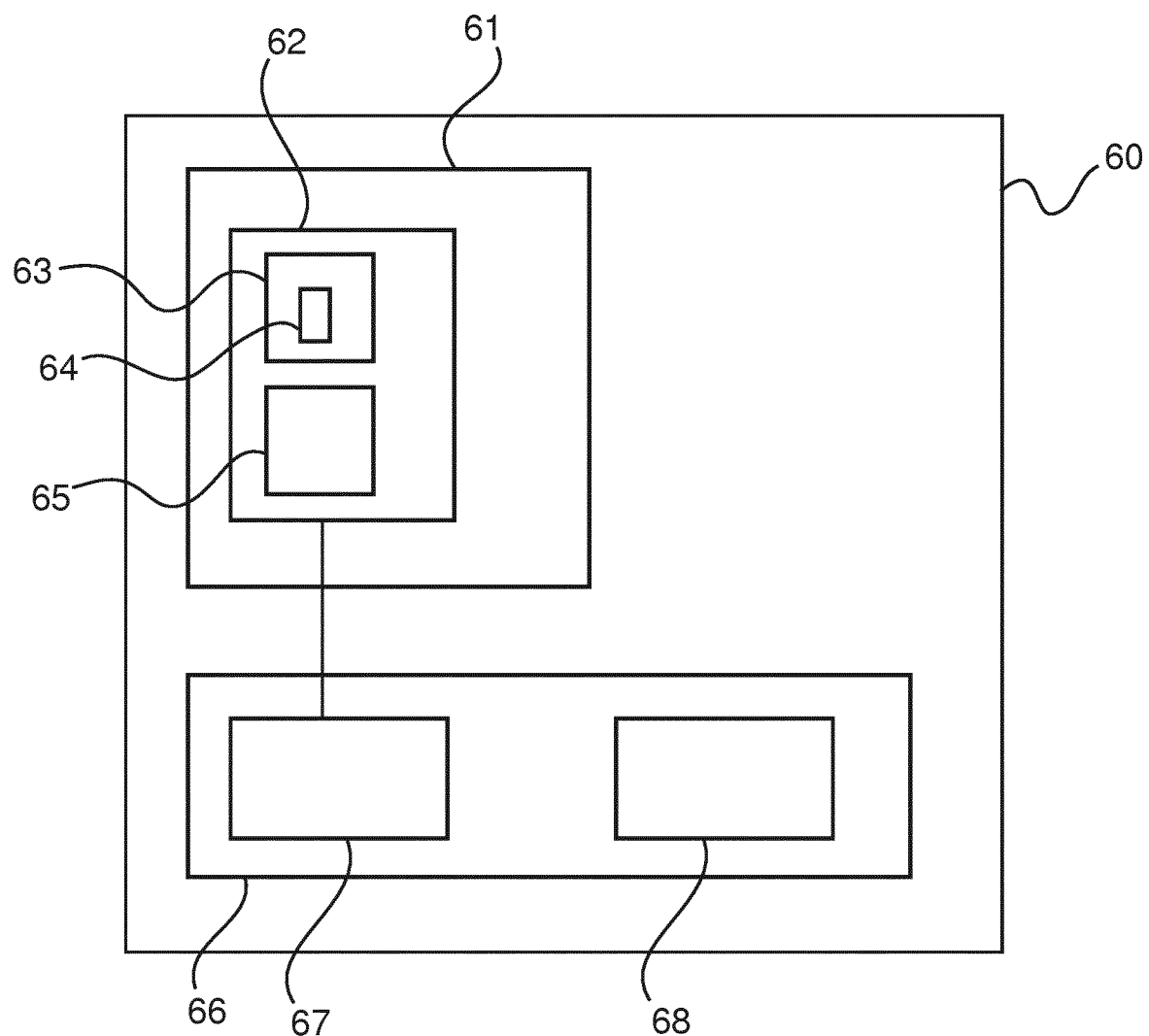
FIG. 6 schematically shows a RT treatment system including a RT treatment planning system according to another exemplary embodiment of the invention.

FIG. 6 schematically shows a RT treatment system 60 including a RT treatment planning system 61 according to another exemplary embodiment of the invention. The radiotherapy treatment system 60 comprises besides the RT treatment planning system 61, a radiation treatment apparatus 66 comprising a treatment beam source 67 and a patient support unit 68. The computer 62 of the RT treatment planning system is operably coupled to the radiation treatment apparatus 66 for issuing a control signal to the radiation treatment apparatus for controlling at least one of the operation of the treatment beam source 67 or and the position of the patient support unit 68. Furthermore, the program 64, which is running on the computer 62 or when loaded onto the computer, causes the computer to perform the method steps of the method according to the first aspect of the present invention. The computer 62 comprises also a program storage medium 63 on which the program is stored, and also comprises the AI module 65. The AI module may be a separate calculation unit within the computer or may be realized as a program/algorithm running on the computer 62.

FIG. 7 schematically shows a method step of providing/generating training data 71 for the AI module 65 from several previous patient cases 72 according to another exemplary embodiment of the invention. The training data 71 may form together a training database 70. In particular, the AI module can be trained with a high number of training data 71 that are optimizations which are calculated from other patients' data 72. The optimization with the classical RT treatment planning optimizer is shown in FIG. 7 with step "Optimization" 73. The training data generally comprise training input data 71a, which comprise at least geometric patient data as well as the dose prescription data and the treatment indication data. The training data 71 also comprise training output data 71b, which comprise at least a part of a dependency $C_i(p_i)$ of a RT quality criterion $C_i$ from an adjustment of a RT planning parameter $p_i$. In the embodiment shown in FIG. 7 the quality criterion is exemplarily shown as "DVH Criterion" and the modified planning parameter $p_i$ is the first slider of the three sliders exemplarily shown in FIG. 7.

For a selection of patient cases a specific treatment setup 72a, including dose prescription data and treatment indication data, and a list 72b of quality criteria $C_i$ can be selected. From the medical image sets (CT, MR, etc.) and the segmented organ structures geometrical features 72c are extracted, wherein these geometrical features are embodiments of the geometric patient data as used in the method of the present invention. If desired, each patient case can be described as an m-dimensional vector 72 of numerical values. Such geometrical features may typically be one or more of the following parameters: the organ at risk (OAR) volume, the planning target volume (PTV), the distance OAR-PTV, OAR concavity/convexity, PTV concavity/convexity, overlap histogram (OVH) data, and others.

For each vector 72 dose optimizations 73 for all different parameter combinations can be performed. While in each case the complete resulting dose distribution could be saved, it is much more memory effective to only save the list of the resulting values of the quality criteria $C_i$.

The AI module can then be trained with the plurality of training data 71 originating from several different patient cases. The training input data 71a, as was described before, are provided to the AI module as input. Also the corresponding dependencies $C_i(p_i)$, that were previously calculated by the optimization with the classical RT treatment planning optimizer in step 73, are provided such that the AI module learns existing correlations between these three kinds of input data and the dependencies $C_i(p_i)$. Thus, due to the training the AI module can then predict whether changes in particular sliders/parameters $p_i$ are likely to have a significant impact on important characteristics $C_i$ of the optimization results for new patient data in the form of new geometric patient data and new dose prescription and treatment indication data. This may of course be done for one or several RT quality criteria $C_i$ and one or several RT treatment planning parameters $p_i$.

By using the AI module, the method of the present invention calculates, i.e. predicts, the dependency $C_i(p_i)$ of a radiotherapy (RT) quality criterion $C_i$ from an adjustment of such a radiotherapy planning parameter $p_i$. In this way, the decision making process in RT treatment plan optimization is streamlined by prediction of promising settings of one or more radiotherapy planning parameters $p_i$ before the actual time intensive iterative optimization process is carried out. This is achieved by applying an AI module, which has been trained to predict the specific behaviour of the dose optimization algorithm, i.e. the optimizer, with respect to geometric patient data, dose prescription and treatment indication data.

The invention claimed is:

1. A computer-implemented medical method of predicting a dependency $C_i(p_i)$ of a radiotherapy (RT) quality criterion $C_i$ from an adjustment of a radiotherapy (RT) planning parameter $p_i$, the method comprising:
    providing geometric patient data geometrically describing an area of a patient, which is to be irradiated according to a radiotherapy treatment plan (step S1),
    providing dose prescription data and treatment indication data for said patient (step S2),
    predicting with a trained Artificial Intelligence (AI) module the dependency $C_i(p_i)$ that reflects a change in the radiotherapy quality criterion $C_i$ from the adjustment of the radiotherapy planning parameter $p_i$ when adjusting said radiotherapy planning parameter $p_i$, using the geometric patient data, the dose prescription data and the treatment indication data as input for the AI module (step S3), and
    wherein the radiotherapy (RT) quality criterion $C_i$ is at least one of RT delivery time, complexity of RT quality assurance, a RT dose constraint, a RT volume constraint regarding a volume within the patient, a conformity index describing how well an irradiated area correlates with a planning target volume, a gradient index describing how quickly a RT radiation dose decreases with increasing distance to a target volume, and any combination thereof;
    determining an amended adjustment range of the RT planning parameter $p_i$ based on the predicted dependency Ci (pi), and
    suggesting the amended adjustment range.

2. The method according to claim 1, further comprising:
    determining a plurality of anchor points based on the predicted dependency $C_i(p_i)$ of the radiotherapy quality criterion $C_i$ from the adjustment of the radiotherapy planning parameter $p_i$, wherein each anchor point is a suggested value of said radiotherapy planning parameter $p_i$ for pre-calculating a dose distribution.

3. The method according to claim 2,
    wherein the determination of the anchor points uses a comparison of the predicted dependency $C_i(p_i)$ with a predefined threshold.

4. The method according to claim 2, wherein the step of predicting the dependency $C_i(p_i)$ comprises;
    determining whether within a predefined range of values of said radiotherapy planning parameter $p_i$ a change of a gradient of the dependency $C_i(p_i)$ is above or below a predefined threshold,
    determining a number of the plurality of anchor points depending on whether the change of the gradient of the dependency $C_i(p_i)$ is above or below the predefined threshold.

5. The method according to claim 4,
    wherein a higher number of anchor points are determined when the change of the gradient of the dependency $C_i(p_i)$ is above the threshold as compared to a lower number of anchor points that are determined if the change of the gradient is lower than the predefined threshold.

6. The method according to claim 2, further comprising:
pre-calculating a RT dose distribution for each of the determined anchor points, and
approximating a RT dose distribution and a value for the RT quality criterion $C_i$, for a value of the radiotherapy planning parameter $p_i$, which is not an anchor point, using results of the pre-calculation of the RT dose distribution for the anchor points.

7. The method according to claim 1,
wherein the radiotherapy quality criterion $C_i$ is a qualitative parameter indicative for a radiotherapy dose distribution.

8. The method according to claim 1,
wherein the radiotherapy planning parameter $p_i$ is at least one of a weighting between a RT target and an organ at risk (OAR), a parameter describing normal tissue sparing, a parameter describing a degree of RT modulation, and any combination thereof.

9. The method according to claim 1, wherein the step of suggesting the amended adjustment range to a user further comprises:
adapting a graphical user interface (GUI) of the RT treatment planning software such that the amended adjustment range of the RT planning parameter $p_i$ is displayed to the user.

10. The method according to claim 1, further comprising:
performing a full optimization of the RT treatment plan with the amended adjustment range of the RT planning parameter $p_i$ by using an RT planning optimization algorithm.

11. The method according to claim 1,
wherein the steps of (S1) to (S3) are repeated for a plurality of radiotherapy quality criteria $C_i$ and a plurality of radiotherapy planning parameters $p_i$.

12. The method according to claim 1, further comprising
extracting geometrical features of the area of the patient, which is to be irradiated by radiotherapy, from at least one medical image and/or from organ structures segmented therefrom.

13. The method according to claim 12, further comprising the steps
providing said extracted geometrical features as an m-dimensional patient vector of numerical values, and
using the m-dimensional patient vector as an input for the AI module.

14. The method according to claim 1, further comprising the steps:
providing for a plurality of current values of RT planning parameters $p_j$, and
considering the current values of RT planning parameters $p_j$ when predicting the dependency $C_i$ ($p_i$) with the trained AI module.

15. A non-transitory computer medium comprising instructions, which, when running on at least one processor of at least one computer, causes at least one processor to perform the steps of:
provide geometric patient data geometrically describing an area of a patient, which is to be irradiated according to a radiotherapy treatment plan;
provide dose prescription data and treatment indication data for said patient;
predict with a trained Artificial Intelligence (AI) module a dependency $C_i$ ($p_i$) that reflects a change in a radiotherapy quality criterion $C_j$ from an adjustment of a radiotherapy planning parameter $p_i$ when adjusting said radiotherapy planning parameter $p_i$, using the geometric patient data, the dose prescription data and the treatment indication data as input for the AI module; and
wherein a radiotherapy (RT) quality criterion $C_i$ is at least one of RT delivery time, complexity of RT quality assurance (QA), a RT dose constraint, a RT volume constraint regarding a volume within the patient, a conformity index describing how well an irradiated area correlates with a planning target volume (PTV), a gradient index describing how quickly a RT radiation dose decreases with increasing distance to a target volume, and any combination thereof;
determining an amended adjustment range of the RT planning parameter $p_i$ based on the predicted dependency Ci (pi), and
suggesting the amended adjustment range.

16. A radiotherapy treatment system comprising one or more processors and associated memory operably coupled with the one or more processors, wherein the memory stores instructions that, in response to execution of the instructions by the one or more processors, causes the one or more processor to perform the steps of:
providing geometric patient data geometrically describing an area of a patient, which is to be irradiated according to a radiotherapy treatment plan;
providing dose prescription data and treatment indication data for said patient;
predicting with a trained Artificial Intelligence (AI) module a dependency $C_i$ ($p_i$) that reflects a change in a radiotherapy quality criterion C; from an adjustment of a radiotherapy planning parameter $p_i$ when adjusting said radiotherapy planning parameter $p_i$, using the geometric patient data, the dose prescription data and the treatment indication data as input for the AI module; and
wherein a radiotherapy (RT) quality criterion $C_i$ is at least one of RT delivery time, complexity of RT quality assurance (QA), a RT dose constraint, a RT volume constraint regarding a volume within the patient, a conformity index describing how well an irradiated area correlates with a planning target volume (PTV), a gradient index describing how quickly a RT radiation dose decreases with increasing distance to a target volume, and any combination thereof;
determining an amended adjustment range of the RT planning parameter $p_i$ based on the predicted dependency $C_i$ ($p_i$), and
suggesting the amended adjustment range;
a radiation treatment apparatus comprising a treatment beam source and a patient support unit;
wherein the one or more processors are operably coupled to the radiation treatment apparatus for issuing a control signal to the radiation treatment apparatus for controlling at least one of:
the operation of the treatment beam source or
the position of the patient support unit.

17. A computer-implemented method of predicting a dependency $C_i$ ($p_i$) of a radiotherapy (RT) quality criterion $C_i$ from an adjustment of a radiotherapy (RT) planning parameter $p_i$, comprising:
providing geometric patient data geometrically describing an area of a patient, which is to be irradiated according to a radiotherapy treatment plan,
providing dose prescription data and treatment indication data for said patient, predicting with a trained Artificial Intelligence (AI) module the dependency $C_i(p_i)$ that reflects a change in the radiotherapy quality criterion $C_i$ from the adjustment of a radiotherapy planning parameter $p_i$ when adjusting said radiotherapy planning parameter $p_i$, using the geometric patient data, the dose prescription data and the treatment indication data as input for the AI module and further including:

determining whether within a predefined range of values of said radiotherapy planning parameter $p_i$ a change of a gradient of the dependency $C_i(p_i)$ is above or below a predefined threshold, determining a number of the plurality of anchor points depending on whether the change of the gradient of the dependency $C_i(p_i)$ is above or below the predefined threshold;

wherein the radiotherapy (RT) quality criterion $C_i$ is at least one of RT delivery time, complexity of RT quality assurance (QA), a RT dose constraint, a RT volume constraint regarding a volume within the patient, a conformity index describing how well an irradiated area correlates with a planning target volume (PTV), a gradient index describing how quickly a RT radiation dose decreases with increasing distance to a target volume, and any combination thereof; and, determining a plurality of anchor points based on the predicted dependency $C_i(p_i)$ of the radiotherapy quality criterion $C_i$ from the adjustment of the radiotherapy planning parameter $p_i$, wherein each anchor point is a suggested value of said radiotherapy planning parameter $p_i$ for pre-calculating.

\* \* \* \* \*

UNITED STATES PATENT AND TRADEMARK OFFICE
CERTIFICATE OF CORRECTION

PATENT NO. : 12,285,628 B2
APPLICATION NO. : 17/429839
DATED : April 29, 2025
INVENTOR(S) : Christian Harrer and Wolfgang Ullrich It is certified that error appears in the above-identified patent and that said Letters Patent is hereby corrected as shown below:

In the Specification

In Column 5, Line 42, delete "$p_i$," and insert -- $p_j$, --, therefor.

In Column 20, Line 3, delete "$p_i$," and insert -- $p_j$, --, therefor.

In Column 21, Line 52, delete "$C_i$" and insert -- $C_1$ --, therefor.

In the Claims

In Column 24, Claim 1, Line 13, after "implemented" delete "medical".

In Column 24, Claim 4, Line 57, delete "$p_i$a" and insert -- $p_i$ a --, therefor.

In Column 25, Claim 15, Line 67, delete "$C_j$" and insert -- $C_i$ --, therefor.

Signed and Sealed this
Sixteenth Day of September, 2025

Coke Morgan Stewart
*Acting Director of the United States Patent and Trademark Office*